United States Patent
Yamashita et al.

(10) Patent No.: US 12,268,738 B2
(45) Date of Patent: Apr. 8, 2025

(54) LIQUID SIX COMBINED VACCINE COMPOSITION

(71) Applicant: KM Biologics Co., Ltd., Kumamoto (JP)

(72) Inventors: Shun Yamashita, Kikuchi (JP); Tatsuya Shirai, Kikuchi (JP); Kazuhiro Daimon, Kikuchi (JP); Tomohiro Minoda, Kikuchi (JP); Shinji Akasaki, Kikuchi (JP); Kanae Ishikawa, Kikuchi (JP); Haruna Iwata, Kikuchi (JP)

(73) Assignee: KM BIOLOGICS CO., LTD., Kumamoto (JP)

(*) Notice: Subject to any disclaimer, the term of this patent is extended or adjusted under 35 U.S.C. 154(b) by 0 days.

(21) Appl. No.: 18/287,248

(22) PCT Filed: Apr. 19, 2022

(86) PCT No.: PCT/JP2022/018211
§ 371 (c)(1),
(2) Date: Oct. 17, 2023

(87) PCT Pub. No.: WO2022/224966
PCT Pub. Date: Oct. 27, 2022

(65) Prior Publication Data
US 2024/0197863 A1    Jun. 20, 2024

(30) Foreign Application Priority Data
Apr. 20, 2021 (JP) ................................. 2021-070897

(51) Int. Cl.
A61K 39/39    (2006.01)
A61K 39/00    (2006.01)
(Continued)

(52) U.S. Cl.
CPC ............ *A61K 39/292* (2013.01); *A61K 39/05* (2013.01); *A61K 39/08* (2013.01); *A61K 39/099* (2013.01);
(Continued)

(58) Field of Classification Search
None
See application file for complete search history.

(56) References Cited

U.S. PATENT DOCUMENTS 6,013,264 A    1/2000 Petre et al.
6,333,036 B1   12/2001 Arminjon et al.
(Continued)

FOREIGN PATENT DOCUMENTS

JP    7-508267       9/1995
JP    2015-533148    11/2015
(Continued)

OTHER PUBLICATIONS

Machine translation of Moriyama et al. (WO 2018/074296) Apr. 2018.*
(Continued)

*Primary Examiner* — Shanon A. Foley
(74) *Attorney, Agent, or Firm* — Wenderoth, Lind & Ponack, L.L.P.

(57) ABSTRACT

Provided is a liquid formulation of a six combined vaccine containing DPT-IPV-Hib-HBs, in which a HBs antigen is stably adsorbed and retained to an aluminum adjuvant, and PRP as a Hib antigen is stably coupled and retained to a carrier protein. A method for producing a stable liquid formulation of a six combined vaccine against diphtheria, pertussis, tetanus, polio, *Haemophilus influenzae* type b (Hib), and hepatitis B (HepB), the method comprising the following steps of: (1) mixing diphtheria toxoid (D) and tetanus toxoid (T) with an aluminum adjuvant to produce a
(Continued)

DT adjuvant; (2) mixing a hepatitis B surface (HBs) antigen with the DT adjuvant obtained in step (1) to produce a DT-HBs adjuvant; (3) mixing a pertussis antigen (P) with the DT-HBs adjuvant obtained in step (2) to produce a DPT-HBs adjuvant; (4) mixing inactivated poliovirus (IPV) with the DPT-HBs adjuvant obtained in step (3) to produce a DPT-IPV-HBs adjuvant; (5) adding a succinate phosphate buffer to the DPT-IPV-HBs adjuvant obtained in step (4), and then adding PRP (PRP-T conjugate) as a Hib antigen to produce a mixture of DPT-IPV-Hib-HBs adjuvant and PRP-T conjugate; and (6) adjusting pH of the mixture of DPT-IPV-Hib-HBs adjuvant and PRP-T conjugate obtained in step (5) to 5.4 to 5.9.

8 Claims, 1 Drawing Sheet

(51) Int. Cl.
  *A61K 39/02* (2006.01)
  *A61K 39/05* (2006.01)
  *A61K 39/08* (2006.01)
  *A61K 39/13* (2006.01)
  *A61K 39/145* (2006.01)
  *A61K 39/29* (2006.01)
(52) U.S. Cl.
  CPC ............ *A61K 39/13* (2013.01); *A61K 39/145* (2013.01); *A61K 2039/5252* (2013.01); *A61K 2039/55505* (2013.01); *A61K 2039/55516* (2013.01); *A61K 2039/55544* (2013.01); *A61K 2039/70* (2013.01)

(56) References Cited

U.S. PATENT DOCUMENTS

| | | |
|---|---|---|
| 2014/0370049 A1 | 12/2014 | Bertaux et al. |
| 2015/0273036 A1 | 10/2015 | Tarli et al. |
| 2019/0076635 A1* | 3/2019 | Shimada ........... A61M 37/0015 |
| 2020/0046822 A1 | 2/2020 | Moriyama et al. |
| 2024/0197863 A1* | 6/2024 | Yamashita ........... A61K 39/145 |

FOREIGN PATENT DOCUMENTS

| | | | |
|---|---|---|---|
| JP | 2017-203043 | | 11/2017 |
| WO | 96/37222 | | 11/1996 |
| WO | 99/13906 | | 3/1999 |
| WO | 2018/074296 | | 4/2018 |
| WO | WO 2019/016654 | * | 1/2019 |

OTHER PUBLICATIONS

International Search Report issued Jul. 19, 2022 in corresponding International (PCT) Patent Application No. PCT/JP2022/018211, 2 pages.

International Preliminary Report on Patentability issued Oct. 24, 2023 in corresponding International (PCT) Patent Application No. PCT/JP2022/018211, 5 pages.

A partial translation (machine translation) of non-patent document 1 (Package insert of Quatrovac (registered trademark)), 6 pages.

Chao-Ming Tsai et al., "Quantification of polysaccharide in Haemophilus influenzae type b conjugate and polysaccharide vaccines by high-performance anion-exchange chromatography with pulsed amperometric detection", Vaccine, vol. 12, No. 8, 1994, pp. 700-706, 7 pages.

Q. Paula Lei et al., "Quantitation of low level unconjugated polysaccharide in tetanus toxoid-conjugate vaccine by HPAEC/PAD following rapid separation by deoxycholate/HCl", Journal of Pharmaceutical and Biomedical Analysis, vol. 21, pp. 1087-1091, 2000, 5 pages.

Yoo Tae Hyeon et al., "Measurement of Free Polysaccharide in Tetanus Toxoid-Conjugate Vaccine Using Antibody/Ammonium Sulfate Precipitation", J. Microbiol. Biotechnol, vol. 13, No. 3, pp. 469-472, 2003, 4 pages.

Catalogue of Automated Enzyme Immunoassay System AIA-360, Tosoh Bioscience, 2013, 6 pages.

* cited by examiner

LIQUID SIX COMBINED VACCINE COMPOSITION

TECHNICAL FIELD

The present invention relates to the field of vaccines used for vaccination for children, and relates to a method for producing a stable liquid formulation of a six combined vaccine for protecting against diphtheria, pertussis, tetanus, polio, *Haemophilus influenzae* type b (Hib), and hepatitis B (HepB).

BACKGROUND ART

So far, various types of vaccines for children have been put on the market. In addition to inactivated vaccine against pertussis, diphtheria, tetanus (DPT), measles-rubella combined vaccine, hepatitis B (HepB) vaccine, mumps vaccine, and varicella vaccine, *Haemophilus influenzae* type b (Hib) vaccine, inactivated polio (IPV) vaccine, pneumococcal conjugate vaccine, and rotavirus vaccine have come to be inoculated, and in particular, vaccination schedule in infancy is extremely tight.

In recent years, a combined vaccine capable of simultaneously acquiring a defense ability against a plurality of viruses, bacteria, and the like has been required for a vaccine for children. The combined vaccine is very effective for reducing burden on recipient and improving inoculation rate by minimizing the number of immunizations to be administered.

In Japan, as combined vaccines based on pertussis diphtheria tetanus vaccine (DPT), QUATTROVAC® (KM Biologics Co., Ltd.), TETRABIK® (The Research Foundation for Microbial Diseases of Osaka University), and SQUAREKIDS® (Daiichi Sankyo Company, Limited), which are products obtained by mixing an inactivated polio vaccine with DPT, have been put on the market. These four combined vaccines are liquid formulations in which an antigen inactivated by formaldehyde is adsorbed to an aluminum adjuvant. QUATTROVAC® and TETRABIK® are obtained by inactivating a Sabin strain which is an attenuated strain of poliovirus, whereas SQUAREKIDS® is obtained by inactivating a wild (virulent) strain (Salk strain). In a vaccine for children, an aluminum adjuvant is used because it is less likely to cause side reactions, and aluminum hydroxide or aluminum phosphate is known.

Furthermore, a five combined vaccine obtained by adding Hib antigen (Polyribosyl-Ribitol-Phosphate (PRP)) for Hib vaccine to these four combined vaccines is being developed. For liquid formulation of a five combined vaccine composed of DPT-IPV-Hib, coupling retention of PRP conjugated to a carrier protein, that is, suppression of detachment is a technical problem, and a production method for solving this problem is disclosed in Patent Document 1. A specific production method is not described in Example 6 of this document, but details are described in Non-patent Document 1. First, pertussis antigen (P) is purified and inactivated with formalin. Next, diphtheria toxoid (D) is adsorbed on an aluminum gel, and separately, tetanus toxoid (T) is adsorbed on an aluminum gel. Next, poliovirus is purified and inactivated with formalin (IPV). Finally, a mixture of them is a DPT-IPV adjuvant, and by further adding PRP conjugated to tetanus toxoid (T) (PRP-T conjugate), a five combined vaccine composed of DPT-IPV-Hib can be prepared (Patent Document 1, Non-patent Document 1).

Globally, as six combined vaccines composed of DPT-IPV-Hib-HBs obtained by further adding hepatitis B surface (HBs) antigen for hepatitis B vaccine to the five combined vaccine, Infanrix-Hexa (GlaxoSmithKline) as a kit formulation, and Hexamine/Hexyon (Sanofi) and Vaxelis (Sanofi-MSD) as liquid formulations are approved. Infanrix-Hexa is a kit formulation including a solution in which DPT-IPV-HBs inactivated with formaldehyde is adsorbed to an aluminum hydroxide adjuvant and a freeze-dried product in which PRP as a Hib antigen is adsorbed to an aluminum phosphate adjuvant. On the other hand, Hexacima/Hexyon and Vaxelis are liquid formulations in which an antigen inactivated with formaldehyde or glutaraldehyde is adsorbed to an aluminum hydroxide adjuvant.

Patent Document 2 discloses a liquid six combined vaccine containing DPT-IPV-Hib-HBs (these antigens are adsorbed on an aluminum salt). Patent Document 2 also describes that antibody titer of Hib conjugated to tetanus protein tends to lose its immunogenicity over time when PRP is adsorbed to an aluminum salt. In order to solve this problem, Patent Document 2 also describes that by adding an anion, particularly a phosphate ion, a carbonate ion or a citrate ion, Hib antigen (PRP) can be prevented from being detached from aluminum hydroxide oxide, and its immunogenicity is maintained. Patent Document 3 describes the same. On the other hand, Patent Document 4 describes that addition of anion desorbs a HBs antigen when the HBs antigen is adsorbed to aluminum hydroxide oxide.

Patent Document 4 discloses a method for preparing a liquid six combined vaccine containing aluminum hydroxide oxide, a HBs antigen, and a Hib antigen conjugated with a carrier protein, in which the HBs antigen remains adsorbed to the aluminum hydroxide oxide, but the Hib antigen remains unadsorbed. The method for preparing a liquid combined vaccine disclosed in Patent Document 4 is a preparation method including first adsorbing a HBs antigen to aluminum hydroxide oxide to obtain a HBs antigen/aluminum hydroxide oxide complex, and then mixing the HBs antigen/aluminum hydroxide oxide complex with a Hib antigen in the presence of a cationic amino acid at a concentration of at least 100 mg/L and a phosphate ion at a concentration of 35 to 45 mmol/L. In Examples of Patent Document 4, it is described that the adsorption ratio of HBs antigen to an aluminum gel was 95 to 98% at the time of preparation, the adsorption ratio of HBs antigen in 5° C. storage stability test was only reduced to 88 to 91% at 9 months and 78 to 86% at 22 months, and non-adsorption of PRP to the aluminum gel was 20.0 to 22.6 µg/mL at the time of preparation, and non-adsorption of PRP in the 5° C. storage stability test was 23 to 27.0 µg/mL at 9 months and 19.9 to 23.9 µg/mL at 22 months, so that there was no significant change.

PRIOR ART DOCUMENTS

Patent Documents

Patent Document 1: WO 2018/074296 A
Patent Document 2: WO 1999/013906 A
Patent Document 3: WO 1996/037222 A
Patent Document 4: JP-A-2017-203043

Non-Patent Documents

Non-patent Document 1: Package insert of QUATTROVAC®
Non-patent Document 2: Vaccine 12 (8) (1994) 700-706
Non-patent Document 3: Journal of Pharmaceutical and Biomedical Analysis 21 (6) (2000) 1087-1091

Non-patent Document 4: Journal of Microbiology and Biotechnology (2003), 13 (3), 469-472

Non-patent Document 5: Catalogue of AUTOMATED ENZYME IMMUNOASSAY SYSTEM AIA-360

SUMMARY OF THE INVENTION

Problems to be Solved by the Invention

For liquid formulation of a six combined vaccine composed of DPT-IPV-Hib-HBs, adsorption retention of a HBs antigen to an aluminum adjuvant and suppression of detachment of PRP as a Hib antigen from a carrier protein are technical problems.

An object of the present invention is to provide a liquid formulation of a six combined vaccine containing DPT-IPV-Hib-HBs, in which a HBs antigen is stably adsorbed and retained to an aluminum adjuvant, and PRP as a Hib antigen is stably coupled and retained to a carrier protein.

Solutions to the Problems

As a result of intensive studies to solve the above problems, the present inventors have found that the HBs antigen is stably adsorbed and retained to the aluminum adjuvant and the PRP is stably coupled and retained by optimizing the final addition concentration of phosphoric acid and pH, thereby completing the present invention.

Therefore, the present invention includes the followings.

[1] A method for producing a stable liquid formulation of a six combined vaccine against diphtheria, pertussis, tetanus, polio, *Haemophilus influenzae* type b (Hib), and hepatitis B (HepB), the method including the following steps of:
  (1) mixing diphtheria toxoid (D) and tetanus toxoid (T) with an aluminum adjuvant to produce a DT adjuvant;
  (2) mixing a hepatitis B surface (HBs) antigen with the DT adjuvant obtained in step (1) to produce a DT-HBs adjuvant;
  (3) mixing a pertussis antigen (P) with the DT-HBs adjuvant obtained in step (2) to produce a DPT-HBs adjuvant;
  (4) mixing inactivated poliovirus (IPV) with the DPT-HBs adjuvant obtained in step (3) to produce a DPT-IPV-HBs adjuvant;
  (5) adding a succinate phosphate buffer to the DPT-IPV-HBs adjuvant obtained in step (4), and then adding PRP (PRP-T conjugate) as a Hib antigen to produce a mixture of DPT-IPV-Hib-HBs adjuvant and PRP-T conjugate; and
  (6) adjusting pH of the mixture of DPT-IPV-Hib-HBs adjuvant and PRP-T conjugate obtained in step (5) to 5.4 to 5.9.

[2] The method according to [1], in which the aluminum adjuvant is an aluminum phosphate gel.

[3] The method according to [1] or [2], in which an amount of the aluminum adjuvant added is 200 to 400 µg/dose.

[4] The method according to any one of [1] to [3], in which in step (5), the succinate phosphate buffer (pH 5.5) is added so that an addition concentration of phosphoric acid is 2 to 8 mmol/L in terms of final concentration.

[5] The method according to [3] or [4], in which the amount of the aluminum adjuvant added is 200 µg/dose, and the addition concentration of phosphoric acid is 2 to 6 mmol/L in terms of final concentration.

[6] The method according to [3] or [4], in which the amount of the aluminum adjuvant added is 300 µg/dose, and the addition concentration of phosphoric acid is 3 to 6 mmol/L in terms of final concentration.

[7] The method according to [3] or [4], in which the amount of the aluminum adjuvant added is 400 µg/dose, and the addition concentration of phosphoric acid is 6 to 8 mmol/L in terms of final concentration.

[8] The method according to any one of [1] to [7], in which an adsorption ratio of HBs antigen to the aluminum adjuvant is 99% or more, and a free PRP content of Hib is less than 20%.

[9] A stable liquid formulation of a six combined vaccine produced by the method according to any one of [1] to [8].

Effects of the Invention

According to the method of the present invention, it is possible to obtain a stable liquid formulation of a six combined vaccine having a HBs antigen adsorption ratio to an aluminum adjuvant of 99% or more and a free PRP content of Hib coupled to a carrier protein of less than 20%. The stable liquid formulation of the six combined vaccine produced by the method of the present invention can provide a sufficient antibody titer (immunogenicity) against six bacteria or viruses required for vaccination.

DETAILED DESCRIPTION

Hereinafter, preferred embodiments of the present invention will be described in detail. However, the present invention is not limited to the following embodiments.

The present invention relates to a method for producing a stable liquid formulation of a six combined vaccine against diphtheria, pertussis, tetanus, polio, *Haemophilus influenzae* type b (Hib), and hepatitis B (HepB), which makes it possible to provide a stable liquid vaccine composition having a HBs antigen adsorption ratio to an aluminum adjuvant of 99% or more and a free PRP content of Hib coupled to a carrier protein of less than 20%, the method including the following steps of:
  (1) mixing diphtheria toxoid (D) and tetanus toxoid (T) with an aluminum adjuvant to produce a DT adjuvant;
  (2) mixing a hepatitis B surface (HBs) antigen with the DT adjuvant obtained in step (1) to produce a DT-HBs adjuvant;
  (3) mixing a pertussis antigen (P) with the DT-HBs adjuvant obtained in step (2) to produce a DPT-HBs adjuvant;
  (4) mixing inactivated poliovirus (IPV) with the DPT-HBs adjuvant obtained in step (3) to produce a DPT-IPV-HBs adjuvant;
  (5) adding a succinate phosphate buffer to the DPT-IPV-HBs adjuvant obtained in step (4), and then adding PRP (PRP-T conjugate) as a Hib antigen to produce a mixture of DPT-IPV-Hib-HBs adjuvant and PRP-T conjugate; and (6) adjusting pH of the mixture of DPT-IPV-Hib-HBs adjuvant and PRP-T conjugate obtained in step (5) to 5.4 to 5.9.

In the production method of the present invention, it is preferable to use an aluminum phosphate gel as the aluminum adjuvant. As the aluminum adjuvant, aluminum hydroxide (synonymous with aluminum hydroxide oxide) and the like are also known in addition to aluminum phosphate, but it is preferable to use an aluminum phosphate gel in order to obtain a stable liquid vaccine composition having a HBs antigen adsorption ratio to the aluminum adjuvant of 99% or more and a free PRP content of Hib antigen coupled to the carrier protein of less than 20%. Also, the amount of the aluminum adjuvant added may be in the range of 200 to 400 μg/dose, but is not limited thereto. Furthermore, the adsorption ratio of the PRP-T conjugate coupled to the carrier protein to the aluminum phosphate gel is preferably 30% or less.

In the production method of the present invention, as antigens of the six combined vaccine for diphtheria, pertussis, tetanus, polio, *Haemophilus influenzae* type b (Hib), and hepatitis B (HepB), diphtheria toxoid (D), tetanus toxoid (T), hepatitis B surface (HBs) antigen, pertussis antigen (P), inactivated poliovirus (IPV), and PRP as a Hib antigen are used, but any antigens known to those skilled in the art can also be used. As the PRP as a Hib antigen, for example, PRP-T conjugate can be used.

Step (1):

In step (1), diphtheria toxoid (D) and tetanus toxoid (T) are adsorbed to an aluminum adjuvant to produce a DT adjuvant. As the aluminum adjuvant, it is preferable to use an aluminum phosphate gel as described above. The tetanus toxoid is required to have a purity exceeding 1,000 Lf (Limit of flocculation)/mg PN by WHO standards. In addition, the standard of Hib conjugate vaccine of European Pharmacopoeia (EP) is >1,500 Lf/mg PN. As a method for purifying tetanus toxoid, ammonium sulfate precipitation, trichloroacetic acid precipitation, column chromatography (gel filtration chromatography, affinity chromatography), salting-out, dialysis, and the like are used.

Step (2):

In step (2), a hepatitis B surface (HBs) antigen is mixed with the DT adjuvant obtained in step (1), and the mixture is left at 15 to 30° C. for 40 to 96 hours to produce a DT-HBs adjuvant.

Step (3):

In step (3), a pertussis antigen (P) is mixed with the DT-HBs adjuvant obtained in step (2) to produce a DPT-HBs adjuvant.

Step (4):

In step (4), inactivated poliovirus (IPV) is mixed with the DPT-HBs adjuvant obtained in step (3) to produce a DPT-IPV-HBs adjuvant.

Step (5):

In step (5), a succinate phosphate buffer is added to the DPT-IPV-HBs adjuvant obtained in step (4), and then PRP as a Hib antigen, for example, PRP-T conjugate is added to produce a mixture of DPT-IPV-Hib-HBs adjuvant and PRP-T conjugate. The succinate phosphate buffer is added in step (5) in order to adjust the final addition concentration of the phosphoric acid according to the amount of the aluminum adjuvant added. That is, the succinate phosphate buffer (pH 5.5) is added so that the addition concentration of phosphoric acid is 2 to 8 mmol/L in terms of final concentration. For example, when the amount of the aluminum adjuvant added is 200 μg/dose, the succinate phosphate buffer (pH 5.5) is added so that the addition concentration of phosphoric acid is 2 to 6 mmol/L in terms of final concentration. When the amount of the aluminum adjuvant added is 300 μg/dose, the succinate phosphate buffer (pH 5.5) is added so that the addition concentration of phosphoric acid is 3 to 6 mmol/L in terms of final concentration. When the amount of the aluminum adjuvant added is 400 μg/dose, the succinate phosphate buffer (pH 5.5) is added so that the addition concentration of phosphoric acid is 6 to 8 mmol/L in terms of final concentration.

In the present invention, as PRP as a Hib antigen, a PRP conjugate in which PRP and a carrier protein are coupled can be used. It is known that an antibody against PRP, which is a capsular polysaccharide of Hib, is effective in protecting against Hib infection, but a Hib vaccine based only on a PRP component is T cell independent, and therefore is insufficient in effect for infants less than 18 months of age with an immature immune system. Therefore, a conjugate vaccine in which a carrier protein is conjugated (coupled) to PRP to make it T cell dependent has been developed and used for infants.

Conjugated vaccines in which polysaccharide such as PRP is coupled to a carrier protein are known. The PRP conjugate can be prepared by known coupling techniques. For example, PRP may be coupled via a thioether linkage. In this coupling method, PRP is activated with 1-cyano-4-(dimethylamino)pyridine tetrafluoroborate (CDAP) to form a cyanate ester. The PRP thus activated can be coupled to an amino group of the carrier protein directly or via a spacer group. Preferably, the cyanate ester is coupled with hexanediamine, and the amino-derivatized polysaccharide is conjugated to the carrier protein using heteroligation chemistry involving formation of thioether linkage. In addition to the above, a conjugate can also be prepared by reductive amination method. Yet another method includes a method in which a cyanogen bromide (CNBr)-activated polysaccharide derivatized with adipic acid dihydrazide (ADH) is coupled to a carrier protein by carbodiimide condensation. As PRP used here, as described in Patent Document 1, PRP having a lower molecular weight than native PRP may be used.

The carrier protein includes tetanus toxoid, pertussis toxoid, diphtheria toxoid, a genetic variant of diphtheria toxoid CRM197, non-capsulated *Haemophilus influenzae* D antigen, outer membrane protein (OMP) of *Neisseria meningitidis* group B, and the like. A typical carrier protein for PRP conjugate is tetanus toxoid. When tetanus toxoid is used as a carrier protein, it is used at a purity of 1,000 Lf/mg PN or more in accordance with WHO standards. In the method of the present invention, the purity of tetanus toxoid is preferably higher, and is preferably 2,500 to 3,500 Lf/mg PN. The purity is more preferably 2,900 to 3,300 Lf/mg PN.

Step (6):

In step (6), when the pH of the mixture of DPT-IPV-Hib-HBs adjuvant and PRP-T conjugate obtained in step (5) is not in the range of 5.4 to 5.9, a pH adjuster is added to adjust the pH to 5.4 to 5.9. In order to obtain a stable liquid vaccine composition having a HBs antigen adsorption ratio to the aluminum adjuvant of 99% or more and a free PRP content of Hib antigen coupled to the carrier protein of less than 20%, the pH of the final product needs to be in the range of 5.4 to 5.9. When the pH of the final product is not in the above range, the desired free PRP content of Hib cannot be obtained.

The free PRP content can be measured by the methods described in Non-patent Documents 2 to 4 and Patent Document 4, and the like. The free PRP content in the present invention was measured by the method described in Example 3 of Patent Document 1. Also, adsorption of HBs antigen to the aluminum adjuvant can be performed by the methods described in Patent Document 4 and Non-patent Document 5, and the like. The amount of HBs antigen adsorbed to the aluminum adjuvant in the present invention was calculated by subtracting the content of HBs antigen in the supernatant from the total content of HBs antigen. The total content of HBs antigen was measured by dissolving the aluminum adjuvant with a chelating agent such as citric acid and using automated enzyme immunoassay system AIA-360 of Tosoh Corporation and a hepatitis B virus surface antigen kit of Tosoh Corporation. In addition, the content of HBs antigen in the supernatant was measured by performing centrifugation, collecting the supernatant containing the non-adsorbed HBs antigen, and using an automated enzyme immunoassay analyzer of Tosoh Corporation and hepatitis B virus surface antigen kit HBsAg of Tosoh Corporation. A long-term storage test when stability is studied is performed under a temperature condition of 5±3° C. or 10° C. or lower avoiding freezing. Alternatively, the stability may be evaluated in an accelerated manner under a higher temperature condition.

The method for producing a stable liquid formulation of a six combined vaccine according to the present invention is performed by steps (1) to (6) as described above, but can also be applied to the case of producing a five combined vaccine prepared by adding a PRP conjugate to a mixture obtained by adding an inactivated poliovirus (Salk-IPV) to a DTP-IPV four combined vaccine (precipitated and purified pertussis-diphtheria-tetanus-inactivated polio (Sabin strain) combined vaccine; for example, QUATTROVAC® manufactured by KM Biologics Co., Ltd.) or a precipitated and purified pertussis-diphtheria-tetanus combined vaccine (KM Biologics Co., Ltd.).

In the method for producing a stable liquid formulation of a six combined vaccine according to the present invention, the composition conditions of the stable liquid formulation are as follows.

Aluminum gel: aluminum concentration of 200 to 400 μg/dose
HBs: 5 to 10 μg/dose
pH: 5.4 to 6.2
Final addition of phosphoric acid: adjusted according to aluminum amount
  Aluminum amount of 400 μg/dose: 6 to 8 mM
  Aluminum amount of 300 μg/dose: 3 to 6 mM
  Aluminum amount of 200 μg/dose: 2 to 6 mM
  (1.5 mM increase to the above concentration when IPV is Sabin strain)

In another aspect, the present invention also provides a stable liquid formulation of a six combined vaccine, which is obtained by the method for producing a stable liquid formulation of a six combined vaccine according to the present invention.

EXAMPLES

Hereinafter, the present invention will be described in detail with reference to examples, but the present invention is not limited to these examples at all.

Comparative Example 1

<Production of Six Combined Vaccine Using Aluminum Phosphate Gel (1)>
PRP conjugated to tetanus toxoid by the method of Patent Document 1 was added to a mixture obtained by adding an inactivated poliovirus (IPV; Salk strain) to a DTP-IPV four combined vaccine (precipitated and purified pertussis-diphtheria-tetanus-inactivated polio (Sabin strain) combined vaccine; QUATTROVAC® manufactured by KM Biologics Co., Ltd.) or a precipitated and purified pertussis-diphtheria-tetanus combined vaccine (manufactured by KM Biologics Co., Ltd.) to prepare a five combined vaccine. An aluminum phosphate adjuvant was used as an adjuvant. A HBs antigen was added to the obtained five combined vaccine to obtain a six combined vaccine composed of DPT-IPV-Hib-HBs. As a result of examining the HBs adsorption ratio of the obtained six combined vaccine, it was found to be less than 10%, and the HBs antigen was not adsorbed to the adjuvant.

Comparative Example 2

<Production of Six Combined Vaccine Using Aluminum Phosphate Gel (2)>
A five combined vaccine was prepared in the same manner as in Comparative Example 1. The obtained five combined vaccine was mixed with a HBs vaccine in which a HBs antigen was adsorbed to an aluminum phosphate adjuvant to obtain a six combined vaccine composed of DPT-IPV-Hib-HBs. As a result of examining the HBs adsorption ratio of the HBs antigen to the adjuvant and the free PRP content of the obtained six combined vaccine, the HBs adsorption ratio of the HBs antigen to the adjuvant was improved to 96% or more, but was still insufficient, and the free PRP content was also increased to 25% or more.

Comparative Example 3

<Production of Six Combined Vaccine Using Aluminum Phosphate Gel>
A five combined vaccine was prepared in the same manner as in Comparative Example 1. The obtained five combined vaccine was mixed with a HBs vaccine in which a HBs antigen was adsorbed to an aluminum phosphate adjuvant to obtain a six combined vaccine composed of DPT-IPV-Hib-HBs. At this time, the aluminum phosphate content was set to 300 μg/dose, and the final addition concentration of phosphoric acid was set to 2 mmol/L. As a result of examining the HBs adsorption ratio of the HBs antigen to the adjuvant and the free PRP content of the obtained six combined vaccine, the HBs adsorption ratio was improved to 99% or more, but the free PRP content was increased to 60% or more.

Example 1

Figure 1:
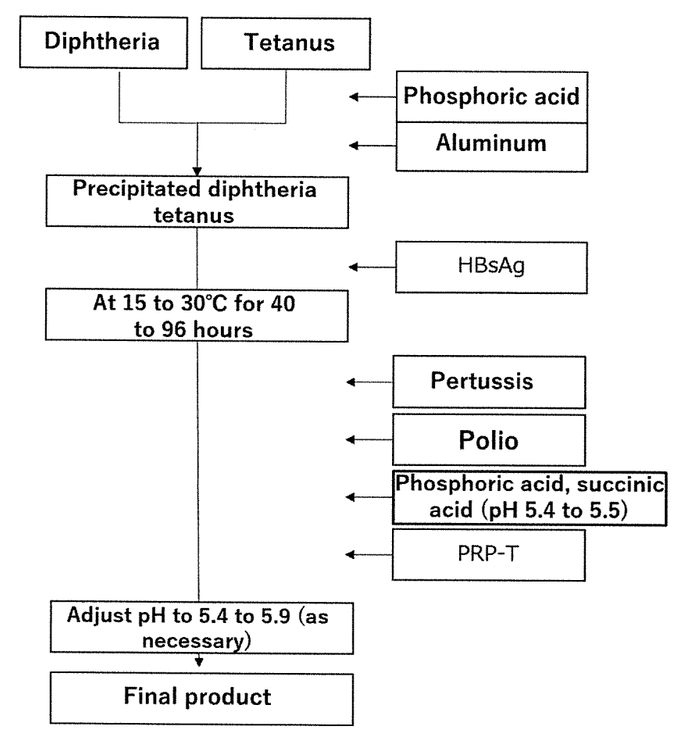
FIG. 1 is a schematic diagram showing an outline of a method for producing a stable liquid formulation of a six combined vaccine according to the present invention.

<Production of Stable Liquid Formulation of Six Combined Vaccine>
A production scheme of a method for producing a stable liquid formulation of a six combined vaccine according to the present invention is shown in FIG. 1. A stable liquid formulation of a six combined vaccine was produced as follows with an aluminum phosphate content of 300 μg/dose.
Adsorption of Diphtheria Toxoid, Tetanus Toxoid to Aluminum Phosphate Gel:
Diphtheria toxoid and tetanus toxoid (diphtheria: 600 Lf/mL, tetanus: 31.2 Lf/mL, ¼ amount of the prepared amount) were mixed with aluminum phosphate gel (final concentration 1.8 mg/mL) and adsorbed. This adsorbed product was used as a precipitated diphtheria-tetanus combined vaccine.

Adsorption of HBs Stock Solution to Precipitated Diphtheria-Tetanus Combined Vaccine:

25 to 50 μg/mL of HBs antigen (⅕ amount of the precipitated diphtheria-tetanus combined vaccine) was added to the precipitated diphtheria-tetanus combined vaccine, and the mixture was allowed to stand at 15 to 30° C. for 40 hours to 96 hours to adsorb HBs.

Preparation of Final Product:

To the above product was added purified pertussis antigen (⅓ amount of final product), polio vaccine trivalent bulk (hereinafter, polio; type 1:type 2:type 3=30:1000:1000 DU (D-antigen unit)/mL, ¹⁄₁₀ amount of final product), succinate phosphate buffer (pH 5.5, addition concentration of phosphoric acid is equivalent to 4.5 mmol/L in terms of final concentration; and is equivalent to 6.0 mmol/L when Sabin IPV is used), and Hib drug substance (hereinafter, PRP-T conjugate: PRP conjugated to tetanus toxoid (T) by the method of Patent Document 1), and the pH was confirmed to be in the range of 5.4 to 5.9. When the pH was out of this range, the pH was adjusted using a hydrochloric acid solution or a sodium hydroxide solution so as to fall within this range. Also, as a result of analyzing the final product, the adsorption ratio of PRP-T conjugate to the aluminum phosphate gel was 30% or less.

The composition of the liquid six combined vaccine formulation (DPT-IPV-Hib-HBs) obtained at this time is shown in Table 1.

TABLE 2

| Specimen | pH | Free PRP content | | |
|---|---|---|---|---|
| | | Immediately after preparation (%) | 37° C. - after 2 weeks (%) | 37° C. - after 4 weeks (%) |
| DPT-IPV (Sabin)-Hib-HBs | 5.0 | 6.7 | 34.9 | 44.3 |
| | 5.2 | 6.8 | 22.3 | 29.2 |
| | 5.4 | 6.3 | 19.5 | 24.5 |
| | 5.6 | 6.6 | 15.6 | 22.1 |
| | 5.8 | 6.6 | 15.6 | 22.3 |
| | 6.0 | 6.7 | 16.9 | 23.5 |
| | 5.7 | 4.8 | 13.9 | 21.2 |
| | 6.2 | 5.0 | 19.4 | 31.9 |
| | 6.3 | 4.7 | 23.5 | 39.0 |
| | 6.7 | 4.8 | 36.7 | 57.0 |
| | 6.7 | 4.6 | 35.5 | 57.9 |
| | 6.6 | 4.5 | 31.7 | 50.3 |
| | 7.0 | 4.9 | 54.8 | 75.3 |

Example 3

<Effect of Aluminum Content and Amount of HBs on Efficacy in Cynomolgus Monkeys>

In order to examine the effect of the amount of aluminum gel and the amount of HBs on the efficacy as a vaccine in the method for producing a liquid six combined vaccine formulation (DPT-IPV-Hib-HBs) found in Example 1, the vaccine

TABLE 1

| Formulation purpose | Component | Quantity (0.5 mL) |
|---|---|---|
| Active ingredient | Fraction of pertussis protective antigen | 4 Units or more |
| Active ingredient | Diphtheria toxoid | 16.7 Lf or less |
| Active ingredient | Tetanus toxoid | 6.7 Lf or less |
| Active ingredient | Inactivated poliovirus type 1 (for Sabin strain)** | 1.5 DU |
| Active ingredient | Inactivated poliovirus type 2 (for Sabin strain)** | 50 DU |
| Active ingredient | Inactivated poliovirus type 3 (for Sabin strain)** | 50 DU |
| Active ingredient | Tetanus toxoid conjugated Haemophilus influenzae type b polysaccharide (as amount of polysaccharide) | 10 μg |
| Active ingredient | HBs antigen | 5 to 10 μg |
| Isotonizing agent | Sodium chloride | 2.38 mg |
| Isotonizing agent | Sodium hydrogen phosphate*** | 0.83 mg |
| Isotonizing agent | Sodium dihydrogen phosphate**** | 1.40 mg |
| Isotonizing agent | Succinic acid | 0.26 mg |
| Isotonizing agent | Disodium succinate hexahydrate | 2.11 mg |
| Stabilizer | Glucose | 0.33 mg |
| Stabilizer | L-Lysine hydrochloride | 0.05 mg or less |
| Inactivating agent | Formalin (as formaldehyde) | 0.1 mg or less |
| Immunopotentiator* | Aluminum chloride | 3.5 mg or less |
| Immunopotentiator* | Sodium hydroxide | 1.6 mg or less |
| Stabilizer | Medium 199 (Ca, Mg, phosphate, phenol red free) | 0.9 mg |
| pH Adjuster | Hydrochloric acid | q.s. |

(Note)
*Material of aluminum gel
**For Salk IPV, type 1:type 2:type 3 was 40:4:32 (unit: DU/0.5 mL).
***Disodium hydrogen phosphate dodecahydrate
****Sodium dihydrogen phosphate dihydrate Example 2

<Effect of pH on Free PRP Content>

For the liquid six combined vaccine formulation (DPT-IPV-Hib-HBs) obtained in Example 1, the effect of pH on the free PRP content was examined. The results are shown in Table 2. The aluminum phosphate content was 300 μg/dose. As is clear from the results shown in Table 2, when the pH was out of the range of 5.4 to 6.2 at 37° ° C. after 2 weeks, the free PRP content was increased, so that it was suggested that the release was promoted.

formulation was administered to cynomolgus monkeys (country of origin: Cambodia, 31 to 35 months old male, 31 to 37 months old female). Blood was collected at the fourth week after inoculation, and serum was collected. The antibody titer was measured by ELISA or EIA using AIA360® (Tosoh Corporation) using each of vaccine antigens prepared autologously from the obtained serum. The results are shown in Tables 3 and 4. In the table, ratios to a control group (simultaneous inoculation of QUATTROVAC® (KM Biologics Co., Ltd.), BIMMUGEN® (KM Biologics Co., Ltd.), and ACTHIB® (Sanofi Pasteur)) inoculated with a combination of approved drugs are shown.

In the composition of an aluminum amount of 100 µg/dose and a HBs amount of 5 µg/dose, the antibody titer was higher than or equal to the control group after priming, but showed a low value of about 0.2 after boosting. On the other hand, in an aluminum amount of 200 µg/dose or more, the control group ratio showed a value of 1 or more after boosting in all doses of HBs. Since antibody titers other than HBs were all equal to or higher than those of the control group, only No. 3 in Table 3 was shown in Table 4.

TABLE 3

| No. | Aluminum amount (µg/dose) | HBs amount (µg/dose) | Anti-HBs antibody titer after priming (Control group ratio) | Anti-HBs antibody titer after boosting (Control group ratio) |
|---|---|---|---|---|
| 1 | 100 | 5 | 1.59 | 0.23 |
| 2 | 400 | 10 | 5.80 | 4.58 |
| 3 | 300 | 10 | 3.62 | 1.95 |
| 4 | 300 | 5 | 4.12 | 1.76 |
| 5 | 200 | 10 | 4.61 | 1.36 |
| 6 | 200 | 5 | 3.40 | 1.29 |

TABLE 4

| Antigen | Antibody titer after priming (Control group ratio) | Antibody titer after boosting (Control group ratio) |
|---|---|---|
| Diphtheria | 1.30 | 0.93 |
| Tetanus | 1.18 | 1.28 |
| Pertussis, PT | 2.35 | 2.71 |

TABLE 4-continued

| Antigen | Antibody titer after priming (Control group ratio) | Antibody titer after boosting (Control group ratio) |
|---|---|---|
| Pertussis, FHA | 1.39 | 1.34 |
| Polio type 1 (Sabin strain) | 1.19 | 0.95 |
| Polio type 2 (Sabin strain) | 1.27 | 1.04 |
| Polio type 3 (Sabin strain) | 1.29 | 1.04 |
| Hib | 4.47 | 2.95 |

Example 4

<Study on Stability of Six Combined Liquid Formulation>

In order to study the stability of the six combined liquid formulation produced in Example 1 using Salk IPV, the effect of the addition concentration of phosphoric acid in the succinate phosphate buffer solution (pH 5.5) on maintenance of adsorption of HBs and suppression of release of PRP was examined. The results are shown in Tables 5, 6, and 7 for the aluminum amounts of 400 µg/dose, 300 µg/dose, and 200 µg/dose, respectively. The phosphoric acid concentration shown here is an addition amount at a final concentration. When Sabin IPV is used, the addition concentration of phosphoric acid is increased by 1.5 mmol/L.

The free PRP content of the specimens after storage at 37° C. for 2 weeks and the adsorption ratio of HBs were examined. As a result, the condition that the HBs adsorption ratio was 99% or more and the free PRP content was less than 20% was that the added phosphoric acid was 5 to 8 mmol/L when the aluminum amount was 400 µg/dose, the added phosphoric acid was 3 to 6 mmol/L when the aluminum amount was 300 µg/dose, and the added phosphoric acid was 2 to 6 mmol/L when the aluminum amount was 200 µg/dose.

TABLE 5

| No. | Aluminum amount (µg/dose) | Addition amount of phosphoric acid (mmol/L) | HBs adsorption ratio (%) 0 week | HBs adsorption ratio (%) 2 weeks | Free PRP content (%) 0 week | Free PRP content (%) 2 weeks |
|---|---|---|---|---|---|---|
| 1 | 400 | 4 | 99.8 | 99.7 | 4.6 | 20.0 |
| 2 | | 5 | 99.7 | 99.6 | 3.7 | 19.7 |
| 3 | | 6 | 99.7 | 99.7 | 3.7 | 15.3 |
| 4 | | 7 | 99.7 | 99.6 | 3.8 | 13.4 |
| 5 | | 8 | 99.7 | 99.6 | 3.8 | 12.9 |
| 6 | | 9 | 99.7 | 96.9 | 3.7 | 12.4 |
| 7 | | 10 | 99.8 | 95.2 | 4.5 | 15.7 |

TABLE 6

| No. | Aluminum amount (µg/dose) | Addition amount of phosphoric acid (mmol/L) | HBs adsorption ratio (%) 0 week | HBs adsorption ratio (%) 2 weeks | Free PRP content (%) 0 week | Free PRP content (%) 2 weeks |
|---|---|---|---|---|---|---|
| 1 | 300 | 2 | 99.9 | 99.9 | 5.3 | 31.4 |
| 2 | | 3 | 99.9 | 99.9 | 5.5 | 17.8 |
| 3 | | 4 | 99.9 | 99.9 | 5.3 | 17.5 |
| 4 | | 5 | 99.9 | 99.9 | 5.4 | 16.5 |
| 5 | | 6 | 99.9 | 99.9 | 5.1 | 15.9 |
| 6 | | 7 | 99.7 | 98.9 | 4.8 | 14.9 |
| 7 | | 10 | 99.7 | 96.7 | 4.4 | 14.4 |

TABLE 7

| No. | Aluminum amount (µg/dose) | Addition amount of phosphoric acid (mmol/L) | HBs adsorption ratio (%) 0 week | HBs adsorption ratio (%) 2 weeks | Free PRP content (%) 0 week | Free PRP content (%) 2 weeks |
|---|---|---|---|---|---|---|
| 1 | 200 | 1 | 99.9 | 99.9 | 5.3 | 31.6 |
| 2 |  | 2 | 99.9 | 99.9 | 4.8 | 19.0 |
| 3 |  | 3 | 99.9 | 99.9 | 4.9 | 14.9 |
| 4 |  | 4 | 99.9 | 99.9 | 4.7 | 14.6 |
| 5 |  | 5 | 99.9 | 99.9 | 5.0 | 14.5 |
| 6 |  | 6 | 99.9 | 99.7 | 4.6 | 14.1 |

Example 5

<Temporal Change in HBs Adsorption Ratio and Free PRP Content Rate of Six Combined Liquid Formulation>

For the six combined liquid formulation obtained in Example 1, transition of the HBs adsorption ratio and transition of the free PRP content during storage at 5±3° C. are shown in Table 8 and Table 9, respectively. As is clear from the results shown in Table 8 and Table 9, it was found that the six combined liquid formulation produced according to the method of the present invention were stable liquid vaccine compositions, having a HBs antigen adsorption ratio to an aluminum adjuvant of 99% or more and a free PRP content of Hib of less than 20% even after storage at 5±3° ° C. for 24 months.

TABLE 8

| No. | Aluminum amount (µg/dose) | HBs amount (µg/dose) | HBs adsorption ratio (%) At start of storage | 1 month | 2 months | 3 months | 6 months | 9 months | 12 months | 24 months |
|---|---|---|---|---|---|---|---|---|---|---|
| 1 | 400 | 10 | 99.9 | 99.9 | 99.9 | 99.9 | 99.9 | 99.8 | — | — |
| 2 | 300 | 10 | 99.9 | 99.9 | 99.9 | 99.9 | 99.9 | 99.9 | 99.9 | 99.9 |
| 3 | 300 | 5 | 99.8 | 99.8 | 99.8 | 99.8 | 99.8 | 99.8 | 99.8 | 99.8 |
| 4 | 200 | 10 | 99.9 | 99.9 | 99.9 | 99.9 | 99.9 | 99.9 | 99.9 | 99.9 |
| 5 | 200 | 5 | 99.8 | 99.9 | 99.8 | 99.8 | 99.8 | 99.8 | 99.8 | 99.8 |

The test for No. 1 was terminated at 9 months.

TABLE 9

| No. | Aluminum amount (µg/dose) | HBs amount (µg/dose) | Free PRP content (%) At start of storage | 1 month | 2 months | 3 months | 6 months | 9 months | 12 months | 24 months |
|---|---|---|---|---|---|---|---|---|---|---|
| 1 | 400 | 10 | 5.9 | 5.9 | 7.1 | 5.6 | 6.7 | 8.1 | — | — |
| 2 | 300 | 10 | 3.5 | 4.1 | 4.8 | 4.2 | 6.3 | 6.3 | 5.7 | 8.3 |
| 3 | 300 | 5 | 3.6 | 4.5 | 4.5 | 4.3 | 6.3 | 5.9 | 5.5 | 8.3 |
| 4 | 200 | 10 | 3.2 | 3.5 | 4.4 | 4.2 | 5.9 | 5.9 | 4.4 | 8.5 |
| 5 | 200 | 5 | 3.6 | 3.6 | 4.6 | 4.3 | 6.3 | 6.1 | 4.2 | 8.3 |

The test for No. 1 was terminated at 9 months.

INDUSTRIAL APPLICABILITY

The present invention is useful in the field of pharmaceuticals, particularly in the field of vaccines.

The invention claimed is:

1. A method for producing a stable liquid formulation of a six combined vaccine against diphtheria, pertussis, tetanus, polio, *Haemophilus influenzae* type b (Hib), and hepatitis B (HepB), the method comprising the following steps of:

(1) mixing diphtheria toxoid (D) and tetanus toxoid (T) with an aluminum adjuvant to produce a DT adjuvant;

(2) mixing a hepatitis B surface (HBs) antigen with the DT adjuvant obtained in step (1) to produce a DT-HBs adjuvant;

(3) mixing a pertussis antigen (P) with the DT-HBs adjuvant obtained in step (2) to produce a DPT-HBs adjuvant;

(4) mixing inactivated poliovirus (IPV) with the DPT-HBs adjuvant obtained in step (3) to produce a DPT-IPV-HBs adjuvant;

(5) adding a succinate phosphate buffer to the DPT-IPV-HBs adjuvant obtained in step (4), and then adding Polyribosyl-Ribitol-Phosphate (PRP) (Polyribosyl-Ribitol-Phosphate conjugated to tetanus toxoid (PRP-T conjugate) as a Hib antigen to produce a mixture of DPT-IPV-Hib-HBs adjuvant and PRP-T conjugate; and (6) adjusting pH of the mixture of DPT-IPV-Hib-HBs adjuvant and PRP-T conjugate obtained in step (5) to 5.4 to 5.9, wherein the aluminum adjuvant is an aluminum phosphate gel.

2. The method according to claim 1, wherein an amount of the aluminum adjuvant added is 200 to 400 μg/dose.

3. The method according to claim 2, wherein the amount of the aluminum adjuvant added is 200 μg/dose, and the addition concentration of phosphoric acid is 2 to 6 mmol/L in terms of final concentration.

4. The method according to claim 2, wherein the amount of the aluminum adjuvant added is 300 μg/dose, and the addition concentration of phosphoric acid is 3 to 6 mmol/L in terms of final concentration.

5. The method according to claim 2, wherein the amount of the aluminum adjuvant added is 400 μg/dose, and the addition concentration of phosphoric acid is 6 to 8 mmol/L in terms of final concentration.

6. The method according to claim 1, wherein in step (5), the succinate phosphate buffer (pH 5.5) is added so that an addition concentration of phosphoric acid is 2 to 8 mmol/L in terms of final concentration.

7. The method according to claim 1, wherein an adsorption ratio of HBs antigen to the aluminum adjuvant is 99% or more, and a free PRP content of Hib is less than 20%.

8. A stable liquid formulation of a six combined vaccine produced by the method according to claim 1.

* * * * *